United States Patent
Rattray et al.

(10) Patent No.: US 11,241,019 B2
(45) Date of Patent: Feb. 8, 2022

(54) METHOD FOR MAKING CHEESE (71) Applicant: Chr. Hansen A/S, Hoersholm (DK)

(72) Inventors: Fergal Rattray, Valby (DK); Annette Helle Johansen, Copenhagen (DK); Mikkel Laust Broe, Middelfart (DK)

(73) Assignee: CHR. HANSEN A/S, Hoersholm (DK)

(*) Notice: Subject to any disclaimer, the term of this patent is extended or adjusted under 35 U.S.C. 154(b) by 401 days.

(21) Appl. No.: 14/789,623

(22) Filed: Jul. 1, 2015

(65) Prior Publication Data
US 2016/0165911 A1 Jun. 16, 2016

Related U.S. Application Data (63) Continuation of application No. 13/055,438, filed as application No. PCT/EP2008/061413 on Aug. 29, 2008, now abandoned.

(51) Int. Cl.
| | | |
|---|---|---|
| A23C 19/032 | (2006.01) |
| A23C 19/068 | (2006.01) |
| A23C 19/072 | (2006.01) |
| A23C 19/05 | (2006.01) |
| C12N 1/20 | (2006.01) |
| C12R 1/225 | (2006.01) |

(52) U.S. Cl.
CPC ........ A23C 19/0323 (2013.01); A23C 19/054 (2013.01); A23C 19/0688 (2013.01); A23C 19/072 (2013.01); C12N 1/205 (2021.05); A23Y 2220/39 (2013.01); C12R 2001/225 (2021.05)

(58) Field of Classification Search
CPC .............. A23C 19/0323; A23C 19/054; A23C 19/0688; A23C 19/072; C12R 1/225
USPC .......................................................... 426/38
See application file for complete search history.

(56) References Cited

U.S. PATENT DOCUMENTS

| | | | | |
|---|---|---|---|---|
| 4,851,237 A * | 7/1989 | Bussiere | .............. | A23C 19/051 426/39 |
| 2009/0088391 A1 * | 4/2009 | Garault | ................ | A23C 9/1234 514/15.7 |
| 2011/0206805 A1 | 8/2011 | Rattray et al. | | |

FOREIGN PATENT DOCUMENTS

| | | | |
|---|---|---|---|
| EP | 1 820 851 A1 | | 8/2007 |
| EP | 1 820 851 A1 | * | 4/2009 |

OTHER PUBLICATIONS

Madkor, S. A., Tong, P. S., El Soda, M., "Ripening of Cheddar Cheese with Added Attenuated Adjunct Cultures of Lactobacilli," J. Dairy Sci. 83:1684-1691 (2000).*

Fromagex website, "DVS-850 Frozen 500u Product description" available at http://www.fromagex.com/can/english/dvs-850-frozen-500u.*

El Soda, M., Madkor, S. A., Tong, P. S., "Adjunct Cultures: Recent Developments and Potential Significance to the Cheese Industry", J. Dairy Science 83: 609-619 (2000).*

El-Soda et al., "Evaluation of commercial adjuncts for use in cheese ripening: 1. Enzymatic activities and autolytic properties of freeze-shocked adjuncts in buffer system," Milchwissenschaft, vol. 54, No. 2, pp. 85-89, 1999.

Fromagex website, "DVS-850 Frozen 500u Product description," obtained online: http://www.fromagex.com/can/english/dvs-850-frozen-500u, Oct. 3, 2013.

Pieter Walstra et al., Dairy Science & Technology, Second edition, Taylor & Francis, Book, pp. 712 (2006).

W. Tungjaroenchai et al., "Influence of Adjunct Cultures on Ripening of Reduced Fat Edam Cheeses", J. Dairy Sci. 84: 2117-2124 (Oct. 2001).

M. El Soda et al., "Adjunct Cultures: Recent Developments and Potential Significance to the Cheese Industry", J Dairy Science 83: 609-619 (Apr. 2000).

S.A. Madkor et al., "Ripening of Cheese with Added Attenuated Adjunct Cultures of Lactobacilli", J Dairy Science 83: 1684-1691 (Aug. 2000).

Office Action dated Apr. 4, 2013 in U.S. Appl. No. 13/055,438 (US 2011/0206805).

Office Action dated Oct. 9, 2013 in U.S. Appl. No. 13/055,438 (US 2011/0206805).

Office Action dated Jun. 3, 2014 in U.S. Appl. No. 13/055,438 (US 2011/0206805).

Office Action dated Oct. 30, 2014 in U.S. Appl. No. 13/055,438 (US 2011/0206805).

Office Action dated Nov. 26, 2014 in U.S. Appl. No. 13/055,438 (US 2011/0206805).

* cited by examiner

Primary Examiner — Jeffrey P Mornhinweg
(74) Attorney, Agent, or Firm — Foley & Lardner LLP (57) ABSTRACT

The present invention relates to a method for making Cheddar type and Continental type cheese with an adjunct culture comprising a *Lactobacillus helveticus* strain.

14 Claims, 4 Drawing Sheets

METHOD FOR MAKING CHEESE

CROSS REFERENCE TO RELATED APPLICATIONS

The present application is a continuation of U.S. patent application Ser. No. 13/055,438, filed May 3, 2011, which is a U.S. National Stage of PCT/EP2008/061413, filed Aug. 29, 2008.

FIELD OF INVENTION

The present invention relates to a method for making cheese, especially Cheddar type and continental type cheese, with a *Lactobacillus helveticus* culture as adjunct culture.

BACKGROUND OF INVENTION

Cheddar type cheeses are made with either mesophilic cultures or a mixture of mesophilic and thermophilic cultures. They are dry salted after the milling step. An example of a rather traditional Cheddar make is given below to illustrate the manufacturing process (according to Walstra et al, 2006 Dairy Science and Technology/Second edition, Taylor & Francis, page 713): Milk is pasteurized (15 sec/71° C.), filled into the cheese vat with a temperature of 30° C. and pre-acidified with addition of starter culture for 40 min at 30° C. Rennet is added and coagulation process takes 35 min at 30° C. The coagulum is cut (10 min) and during 30 min of stirring the curd/whey is heated up to scalding temperature of 40° C. The scalding temperature is held for 60 further minutes. Then the curd settles, fuses into a compact mass and whey is taken off (30 min). Afterwards, the cheddaring takes place (100 min) where the curd mass is cut into large strips that are piled up and turned. Prior to salting, the curd is milled into small strips. Salt is added and mixed with the curd strips. The salted curd is then filled into moulds and pressed (16 h/2 bars). After a certain drying phase, cheeses are packed and ripened at relatively low temperature such as 8 to 11° C.

Traditionally, cheeses of the continental type are made with mesophile starter cultures. An example of a cheese of the continental type is the Samsø cheese. A Samsø cheese (30% fat in dry matter) is made according to the following steps: Milk is standardized in fat content (e.g. 1.6% fat), pasteurized (20 sec/72° C.) and filled into the cheese vat with a temperature of 31° C. $KNO_3$ and $CaCl_2$ may be added to the milk. Milk is afterwards inoculated with the mesophile starter culture. Rennet is added and coagulation process takes 45 min at 31° C. The coagulum is cut (5 min) and 35% of the whey is drained off. Hot water is added and the scalding is made at 37° C. The stir out phase takes 40 min and afterwards the whey is drained off and the curd is transferred into moulds. The curd is pressed in the moulds at 4 bar, and then at 6 bar for 70 min in total. After a subsequent resting phase cheese temperature falls to 12° C. Subsequently cheeses are salted in a brine (20 hours).

In the manufacturing of fermented milk product there is a constant need for alternative and improved manufacturing method. Such desired methods typically aim at improving the manufacturing process e.g. by reducing cost, increasing speed of the overall process and/or improve characteristics of the final product. Desired product improvements include all known product quality parameters such as taste, texture, flavour etc. In fermented products the manufacturing process includes the addition of a starter culture performing the specific fermentation. In cheese production, the objective of the starter culture is to primarily acidify the raw material, milk. Often, it is not possible to optimize the performance of the primary starter in a way that secures optimal taste/flavour of the final product.

In the case of cheese production, often a ripening step is included in the production process. During the ripening phase proteolysis, amino acid catabolism and lipolysis are key factors for texture and flavour development in the cheese product. The ripening phase should result in the development of the desired organoleptic properties of the cheese in a short time frame. As a result it has been suggested to apply "adjunct cultures" in the manufacturing of fermented milk products aiming at improving the characteristics of the product such as texture and/or flavour. This is of special relevance in reduced-fat or low-fat cheeses. Adjunct cultures are expected to improve the characteristics of the product such as texture and/or flavour but not to interfere with the acidification of milk caused by the primary starter culture. Adjunct cultures influence the cheese ripening process trough their enzymatic systems involving among others proteinases, peptidases, aminopeptidases, aminotransferases, esterases and lipases. The enzymatic potential is species and/or strain dependent.

Adjunct cultures are often *Lactobacillus* strains which are shown to contribute to the flavor development. The use of *Lactobacillus helveticus* as an adjunct culture to cheese has been studied. Nevertheless *Lactobacillus helveticus* as an adjunct culture can only be used at limited inoculation rates due to its impact on the acidification profile. This is especially relevant in cheese technologies where the scalding temperature is high enough to allow significant growth of the thermophile *Lactobacillus helveticus* adjunct culture (as e.g. 40° C. in a Cheddar cheese make). Different approaches were proposed to overcome this problem. One approach is to use attenuated (non viable) adjunct cultures. The most investigated methods for attenuation are of physical character as e.g. heat shock and freeze shock. The drawback of this approach is that the attenuation process is an extra step during culture preparation that has to be carried out either at the culture producer or the cheese producer under reproducible conditions. It should be emphasized that changes in the acidification process during a cheese make will without any further adaptation of the cheese making process impact on whey drainage from the cheese curd, the content of minerals in the curd/cheese and the minimum pH during the cheese make. This has important unwanted consequences on the cheese composition, cheese ripening and the obtained characteristics of the product such as texture and/or flavour.

SUMMARY OF INVENTION

It has surprisingly turned out that it is possible to obtain a *Lactobacillus* adjunct culture which does not influence milk acidification during cheese making. This *Lactobacillus* culture is a mutant of an acidifying strain, and has turned out to be non-acidifying. According hereto, the present inventors have brought forward a method to improve the texture and/or taste and/or flavour of cheeses, especially of the cheddar type and the continental type which method implies using a non-acidifying thermophilic *Lactobacillus helveticus* strain as adjunct culture without influencing milk acidification. The non-acidifying *Lactobacillus helveticus* strains were obtained by mutation of an acidifying mother strain DSM 19500.

During cheese production, the non-acidifying mutants may be added to the cheese milk together with the primary starter cultures.

It was surprisingly observed that the non-acidifying *Lactobacillus helveticus* mutants maintained the mother strain's ability to improve cheese texture and/or taste and/or flavour, especially to debitter cheese and to introduce the typical *Lactobacillus helveticus* "sweet" flavour note in ripened cheese. The mutant was used for the cheese make as a non attenuated adjunct culture, so no extra attenuation process was needed.

In accordance with the surprising finding, the present invention relates to a process for producing cheese (eg full fat, reduced fat and low fat cheese), which comprises:
adding to milk
  a starter culture, such as culture comprising a strain belonging to a genus selected from the group consisting of: *Lactococcus, Leuconostoc, Pediococcus, Streptococcus,* and *Enterococcus*, and
  a non-acidifying *Lactobacillus helveticus* strain as adjunct strain;
  a coagulant, such as a milk-clotting enzyme;
heating the mixture to a temperature (or maintaining the temperature) in the range of 30 to 45 degrees C.

DETAILED DESCRIPTION OF INVENTION

In a first aspect, the present invention relates to a process for producing cheese, which comprises:
adding to milk
  a starter culture, such as culture comprising an acidifying strain belonging to a genus selected from the group consisting of: *Lactococcus, Leuconostoc, Pediococcus, Streptococcus,* and *Enterococcus*; and
  an adjunct culture comprising a non-acidifying *Lactobacillus helveticus* strain; and
heating the mixture to a temperature (or maintaining the temperature) in the range of 30 to 45 degrees C., such as in the range 35 to 43 degrees C. or in the range 37-43 degrees C.

An interesting embodiment relates to a process for producing cheese (including reduced and low fat cheese), which comprises:
adding to milk
  a starter culture, such as culture comprising an acidifying strain belonging to a genus selected from the group consisting of: *Lactococcus, Leuconostoc, Pediococcus, Streptococcus,* and *Enterococcus;*
  an adjunct culture comprising a non-acidifying *Lactobacillus helveticus* strain; and a coagulant, such as a milk-clotting enzyme; and
heating the mixture to a temperature (or maintaining the temperature) in the range of 30 to 45 degrees C., such as in the range 35 to 43 degrees C. or in the range 37-43 degrees C.

An other interesting embodiment relates to a process for producing cheese (including reduced and low fat cheese), which comprises:
adding to milk
  a starter culture, such as culture comprising an acidifying strain belonging to a genus selected from the group consisting of: *Lactococcus, Leuconostoc, Pediococcus, Streptococcus,* and *Enterococcus;*
  an adjunct culture comprising a non-acidifying *Lactobacillus helveticus* strain; and a coagulant, such as a milk-clotting enzyme; and
heating the mixture to a temperature (or maintaining the temperature) in the range of 30 to 45 degrees C., such as in the range 35 to 43 degrees C. or in the range 37-43 degrees C. and holding the mixture at that temperature range for 5 to 70 minutes immediately before whey removal or pre-pressing under whey.

Also, the invention relates to a process for improving the texture and/or taste and/or flavour of cheese, and a process for improving cheese quality, the processes comprising adding to milk
  a lactic acid bacteria culture comprising a strain belonging to a genus selected from the group consisting of: *Lactococcus, Leuconostoc, Pediococcus, Streptococcus,* and *Enterococcus,* and
  a non-acidifying *Lactobacillus helveticus* strain; and;
  a coagulant, such as a milk-clotting enzyme; and
heating the mixture to a temperature (or maintaining the temperature) in the range of 30 to 45 degrees C., such as in the range 35 to 43 degrees C. or in the range 37-43 degrees C.

In a preferred embodiment, the non-acidifying *Lactobacillus helveticus* strain is not able to lower the pH more than 1.5 pH Units (such as more than 1.3) from start pH 6.5 after 10 hours incubation at 37° C. when inoculated from a fresh over night culture at inoculation dose $1.5 \times 10^7$ cfu/ml into 200 ml milk, especially into milk prepared from 9.5% skim milk powder rehydrated in water (heat treated at 140° C./8 sec and 100° C./30 min). Thus, in the most preferred embodiment, the non-acidifying *Lactobacillus helveticus* strain is not able to lower the pH more than 1.3 pH Units from start pH 6.5 after 10 hours incubation at 37° C. when inoculated from a fresh over night culture at inoculation dose $1.5 \times 10^7$ cfu/ml into 200 ml milk prepared from 9.5% skim milk powder rehydrated in water (heat treated at 140° C./8 sec and 100° C./30 min).

The non-acidifying *Lactobacillus helveticus* strain may be a mutant of an acidifying strain (which in the present context is a strain able to lower the pH more than 1.3 (or more than 1.5) pH Units from start pH 6.5 after 10 hours incubation at 37° C. when inoculated from a fresh over night culture at inoculation dose $1.5 \times 10^7$ cfu/ml into 200 ml milk prepared from 9.5% skim milk powder rehydrated in water (heat treated at 140° C./8 sec and 100° C./30 min). In a embodiment, the non-acidifying *Lactobacillus helveticus* strain is a mutant of an acidifying *Lactobacillus helveticus* strain, preferably a mutant having an at least as high cell wall bound protease activity as the mother strain (determined by identical method as disclosed in example 1c). In a presently preferred embodiment, the non-acidifying *Lactobacillus helveticus* strain is a mutant of the acidifying strain DSM 19500, e.g. the mutant DSM19501.

In an important embodiment of the process of the invention, the starter culture is added in an amount of at least $10^3$ CFU per ml milk, and/or the *Lactobacillus helveticus* strain is added in amount of at least $10^4$ (such as at least $10^5$, $10^6$, at least $10^7$ or $10^8$) CFU per ml milk.

In the process of the invention the starter culture may comprise bacteria belonging to a strain selected from the group consisting of: *Lactococcus lactis, Leuconostoc mesenteroides, Pediococcus pentosaceus, Lactobacillus casei, Lactobacillus paracasei, Streptococcus thermophilus, Enterococcus faecium, Lactobacillus delbrueckii* subsp. *bulgaricus, Lactobacillus delbrueckii* subsp. *lactis* and *Lactobacillus acidophilus,* preferably the strain is *Lactococcus lactis* subsp. *lactis, Lactococcus lactis* subsp. *cremoris,* or *Lactococcus lactis* subsp. *lactis* biovar. *diacetylactis.*

The cheese be made by the process may be a cheddar type cheese, or a continental type cheese (eg Gouda, Danbo, Havarti etc), including low-fat cheese, and thus it is presently preferred that no bacteria belonging to the genus *Propionibacterium* are added to the milk, especially in a concentration over $10^2$ cfu per ml, but the process instead comprises the further step of pressing the mixture obtained in the heating step, either before or after salting. The pressed and salted cheese is preferably kept at a temperature in the range of 1 to 25 degrees C., or the pressed and salted cheese is not maintained at a temperature over 25 degrees C. for more than 2 hours.

In an other aspect, the present invention relates to a cheese (including a low-fat cheese) obtainable by the process of any preceding claim, such as a cheddar type cheese.

In the last aspect, the present invention relates to strains that can be used in the process of the invention, and strains that can be used as starting material for a non-acidifying mutant. Thus, the present invention relates to an acidifying *Lactobacillus helveticus* strain selected from the group of DSM19500, DSM 18879, DSM 18880, DSM 18881, DSM 18871, DSM 18872, DSM 18873, DSM 18883, DSM 18884 and the mutants and variants of any of these, esp. non-acidifying mutants and variants, and to the *Lactobacillus helveticus* strain DSM19501 and mutants or variants thereof, such as non-acidifying mutants and variants.

DEFINITIONS

By the term "milk" is understood a composition comprising lacteal secretion obtained from any mammal, such as an animal of a species belonging to the subfamily Bovinae (which includes the domestic cow (Bos taurus) and buffalo); an animal of a species belonging to the subfamily Caprinae (which includes goat and sheep); or an animal of the species Camelidae (which includes camels). Optionally the milk is acidified, e.g. by addition of an acid (such as citric, acetic or lactic acid) or by addition of an acid producing microorganism. The milk may be raw or processed, e.g. by filtering, sterilizing, pasteurizing, homogenizing, fractionating (e.g. reducing the fat content of the milk), etc, or it may be reconstituted dried milk. An important example of "milk" according to the present invention is pasteurized cow's milk. It is understood that the milk may be acidified, mixed or processed before, during and/or after the adding of bacterial cultures.

The term "coagulant" refers to any kind of milk clotting agent, such as a native enzyme derived from microbial, vegetable or animal tissue sources or a milk clotting enzyme provided as a gene product of recombinant cells expressing a milk clotting enzyme of animal or microbial origin. The term includes bovine chymosin purified from abomasum tissue or made by fermentation (e.g. CHY-MAX® or CHY-MAX® M).

The term "cheese" refers to a product prepared by contacting optionally acidified milk (e.g. by means of a lactic acid bacterial culture) with a coagulant, and draining the resultant curd. Cheeses and their preparation are described in "Cheese and Fermented Milk Foods", by Frank V. Kosikowski.

The term "cheese of the cheddar type" should be understood as cheeses of the types such as Cheddar, Territorials, American Cheddar, Monterey Jack and Colby, and/or cheeses made by a process which includes heating the curd to a temperature that does not exceed 45 degrees C. In the present context, cheese of the cheddar type is characterized by:

Fat in Dry matter: 10-60%
Humidity: 34-42%
Salt content: 1.5-2.5%
Cheddaring and subsequent Milling step
Salting after milling but before pressing
Pressing step The term "cheese of the continental type" should be understood as cheeses of the types, such as Gouda, Danbo, Edam, St. Paulin, Raclette, Fontal etc and/or cheeses made by a process which includes heating the curd to a temperature that does not exceed 45 degrees C. In the present context, cheese of the continental type is characterized by:

Fat in Dry matter: 10-60%
Water content: 35-57%
Water in Fat free cheese matter: 53-63%
Salt content: 1-3.5%
Pressing step during cheese manufacture process
Salting after pressing most often in a brine The term "reduced fat cheese" refers to cheese having a fat content reduced to 32% fat in dry matter or less, down to 25% fat in dry matter, and the term "low fat cheese" refers to cheese having a fat content reduced to 25% fat in dry matter or less. The person skilled in the art is familiar with the adjustment of the milk fat content in respect to varying protein content of the milk. Fat content in cheese can be determined after van Gulik method ISO 3433, commonly known by the skilled person of the art. Example for Gouda cheese:

full fat cheese: 45% fat in dry matter/ca. 3.1% fat in milk
reduced fat cheese: 30% fat in dry matter/ca. 1.6% fat in milk
low fat cheese: 15% fat in dry matter/ca. 0.7% fat in milk As used herein the term "lactic acid bacterium" designates a gram-positive, microaerophilic or anaerobic bacterium, which ferments sugars with the production of acids including lactic acid as the predominantly produced acid. The industrially most useful lactic acid bacteria are found among *Lactococcus* spp., *Streptococcus* spp., *Lactobacillus* spp., *Leuconostoc* spp., *Pediococcus* spp. Additionally, lactic acid producing bacteria belonging to the group of the strict anaerobic bacteria, *Bifidobacterium* spp., which are frequently used as food cultures alone or in combination with other lactic acid bacteria, are generally included in the group of lactic acid bacteria. The term "CFU" (or "cfu") is short for cell forming units.

The term "starter culture" relates to any bacterial culture that is suitable for use in milk acidification, especially lactic acid bacteria such as Bifidobacteria, Lactobacilli, Lactococci, Leuconostocs, Micrococci and Pediococci. It will be appreciated that the term starter culture may encompass a culture containing a single strain of bacterium, or more than one bacterial strain. The term may also include genetically modified organisms (GMO's). In any event, the term is well known in the art and the invention extends equally to all known starter cultures. The term includes bacterial cultures containing a strain of a genus selected from the group consisting of *Lactococcus, Lactobacillus, Micrococcus, Leuconostoc, Pediococcus, Streptococcus, Enterococcus*, etc. such as a strain of a species selected from the group consisting of: *Lactococcus lactis* (incl. *Lactococcus lactis* subsp. *lactis, Lactococcus lactis* subsp. *cremoris*, and *Lactococcus lactis* subsp. *lactis* biovar. *diacetylactis*), *Leuconostoc mesenteroides* (incl subsp. *cremoris*), *Pediococcus pentosaceus, Lactobacillus casei* (incl. subsp. *casei*) and *Lactobacillus paracasei* (incl. subsp. *paracasei*), *Streptococcus thermophilus, Enterococcus faecium, Lactobacillus helveticus, Lactobacillus delbrueckii* subsp. *bulgaricus*,

*Lactobacillus delbrueckii* subsp. *lactis* and *Lactobacillus acidophilus*. Other useful bacterial species are *Bifidobacterium* species including *B. bifidum*, *B. lactis* and *B. longum, Streptococcus faecium, Leuconostoc lactis*.

As previous mentioned, lactic acid bacteria are essential in the making of nearly all fermented milk products e.g. cheese, and they are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product. Such cultures are in general referred to as "starter cultures" or "starters".

Commonly used starter culture strains of lactic acid bacteria are generally divided into mesophilic organisms having optimum growth temperatures at about 30 to 35° C. and thermophilic organisms having optimum growth temperatures in the range of about 40 to about 45° C. Typical organisms belonging to the mesophilic group include *Lactococcus lactis* subsp. *lactis, Lactococcus lactis* subsp. *cremoris, Leuconostoc mesenteroides* subsp. *cremoris, Pediococcus pentosaceus, Lactococcus lactis* subsp. *lactis* biovar. *diacetylactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus, Lactobacillus delbrueckii* subsp. *lactis* and *Lactobacillus acidophilus*.

Additionally, species of *Propionibacterium* are used as dairy starter cultures, in particular in the manufacture of cheese.

"Adjunct cultures" are in this context defined as strains of cheese related microorganisms that are added to the cheese milk to improve the sensory quality of cheese in terms of texture and/or taste and/or flavour. Adjuncts cultures are specifically selected for their abilities to improve the sensory quality of cheese and are intentionally added to the cheese milk by the cheese maker at preferably $10^2$ to $10^8$ cfu/ml milk. Adjunct cultures influence the cheese ripening process trough their enzymatic systems involving among others proteinases, peptidases, aminopeptidases, aminotransferases, esterases and lipases. The enzymatic potential is species and/or strain dependent.

Adjunct cultures have become an important tool for the cheese manufacturer in achieving cheeses with improved taste and/or texture and/or flavour. The need to improve flavour development especially in reduced or low-fat cheese has created an increased interest in the utilization of adjunct cultures.

The term "non-acidifying" in the present context refers to a strain that does not lower the pH of (bovine) milk more than 1.5, or presently preferred, not more than 1.3 pH Units from start pH 6.5 after 10 hours incubation at 37° C., preferably under the following conditions:

inoculated from a fresh over night culture at inoculation dose $1.5 \times 10^7$ cfu/ml into (e.g. 200 ml) milk prepared from 9.5% skim milk, e.g powder rehydrated in water, and preferably heat treated at 140° C./8 sec and 100° C./30 min. The person skilled in the art should understood how to incubate the *L. helveticus* strain and assess the strain's acifying properties, and he will find guidance in the assay: assessment of acidification activity of mutants by direct pH measurement in milk, see example 2.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, non-acidifying properties as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant.

In the present context, the term "variant" should be understood as strain which is functionally equivalent to a strain of the invention, e.g. having substantially the same, or improved, non-acidifying properties. Such variants, which may be identified using appropriate screening techniques, are a part of the present invention.

The use of the terms "a" and an and the and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSITS AND EXPERT SOLUTION

The *Lactobacillus helveticus* mother strain was deposited 2007-07-04 at Deutsche Sammlung von Mikroorganismen and Zellkulturen GmbH, Inhoffenstr. 7B, D-38124 Braunschweig (DSM) and given the accession number DSM 19500. The *Lactobacillus helveticus* mutant strain was deposited 2007-07-04 at DSM and given the accession number DSM19501. The deposits were made according to the Budapest treaty on the international recognition of the deposit of microorganisms for the purposes of patent procedure.

The applicant requests that a sample of the deposited microorganisms stated above may only be made available to an expert, until the date on which the patent is granted.

REFERENCES

Walstra et al, 2006 Dairy Science and Technology/Second edition, Taylor & Francis Cheese and Fermented Milk Foods, by Frank V. Kosikowski.

El-Soda et al, 2000. Adjunct cultures: Recent Developments and Potential Significance to the Cheese Industry. Journal of Dairy Science. 83: 609-619.

All references cited in this patent document are hereby incorporated herein in their entirety by reference.

EXPERIMENTAL

Conventional Cheese Manufacturing

Most cheese productions include a pasteurization and fat standardization of cheese milk prior to the inoculation of lactic acid bacteria starter culture (either as liquid bulk or as concentrated bacteria (frozen or freeze-dried), e.g. Chr. Hansen's Direct Vat Set). Starter culture inoculation takes typically place at temperatures from 30 to 35° C. The so-called pre-ripening time may vary between cheese types, but is typically in the range of 10 to 60 min before a coagulant is added to set the milk having a typically setting time in the range of 15 to 60 min.

When the curd is formed it is cut into cubes (typically 5-20 mm) in order to facilitate syneresis of whey and concentration of milk constituents during a gentle agitation. Many cheese varieties undergo an increase of temperatures in the cheese vat (typically 36-45° C.). This is normally done with two purposes: 1) to increase the speed of syneresis and reduced the final moisture in cheese and 2) to affect the starter culture either by increasing the acidification speed of especially thermophilic LAB and/or by inducing lysis of mesophilic LAB. During the process in the cheese vat, parts of the whey may be removed and water may be added. When the curd grains obtain the right texture and acidity (typically pH 5.0 to 5.5) the grains are moulded (with or without whey removed) and pressed into shapes depending on the specific cheese variety. Most cheeses are salted, which can be done either before (typically dry salting) or after (brine-salting) the moulding. Ripening and storage conditions vary between different cheese varieties.

Sensory Analysis

According to International Standards (ISO 5492:1992 Sensory analysis—vocabulary) sensory perception include the attributes "taste", "flavour", "odour" and "aroma". Aroma and odour are primarily associated with the perception by the olfactory organ (nose) prior to and during eating. Taste is defined as the basic tastes perceived by the taste buds in the mouth. Typically, taste is described as "sweet", "sour/acid", "salt" and "bitter". Flavour is defined as a complex combination of the olfactory, gustatory (taste) and trigeminal (feeling) sensations perceived during eating. When food products are to be sensory evaluated it is custom to focus on the perception of taste and flavour.

Thus, when the expression "improved/altered taste and/or flavour" is used herein, it is to be understood as the improved/altered taste and/or flavour as perceived and described by the sensory panel evaluating the cheese of the invention. This should not be taken as an exclusion of possibly altered odour and/or aroma but merely as a simple means to describe the fermented milk product of the invention.

For illustration, in working example 3 herein, one suitable sensory evaluation method is the "Sensory profile". Preferably, the test is performed according to the International Standard (ISO 13299:2003 Sensory analysis—Methodology—General guidance for establishing a sensory profile).

This standard describes a guidance on the steps that are common to all sensory profiling. Sensory profiles can be established for products such as e.g. foods and beverages. Sensory profiling is based on the concept that the sensory impression made by the sample consists of a number of identifiable sensory attributes (descriptors), each of which is present to a larger or smaller degree. The list of relevant sensory descriptors, each with its intensity value, is the sensory profile. Sensory profiling can be used to compare a product/sample with a standard or with other similar products, also across all of the senses. Thus, the method is suitable for the present purpose i.e. evaluate the effect of use of an additional ingredient i.e. an adjunct culture in the production of a fermented milk product.

As will be illustrated in the example 3 herein, the assessors of the sensory panel were able to compare the product made according to the present invention using a non-acidifying *Lactobacillus helveticus* as adjunct culture in comparison to a product made with an acidifying *Lactobacillus helveticus* and the product made without adjunct culture.

Example 1

Generation of Non-Acidifying *Lactobacillus Helveticus* Mutants and Verification of their Acidification Behaviour in Milk a) Generation of Non-Acidifying Mutants from *Lactobacillus Helveticus* DSM19500 by Ethyl Methane Sulphonate (EMS) Mutagenesis From frozen stock ampoule, 100 µl of strain DSM19500 were inoculated into 10 ml M17 broth+1% lactose. The culture was incubated at 37° C. (anaerobic) overnight.

150 µl Ethyl Methane sulphonate were added to the 10 ml overnight culture and the tube was sealed with para-film. The EMS-culture was incubated in a closed incubatorbox at 37° C. rotating slowly for 2 hours. 200 µl EMS-culture was inoculated into 10 ml M17 broth+1% lactose. The culture was incubated at 37° C. (anaerobic) overnight.

200 µl 87% glycerol were added to 1000 µl EMS-overnight-culture, mixed thoroughly and the stocks were stored at minus 80° C. 100 µl sample diluted to $10^{-4}$-$10^{-7}$ was spread on petri-dishes with 20 ml M17 agar+1% w/v lactose+0.5 mg/ml streptomycin sulphate and 100 µl sample diluted to $10^{-4}$-$10^{-7}$ was spread on petri-dishes with 20 ml M17 agar+1% lactose and incubated at 37° C., anaerobically, over night.

The mutagenesis frequency was checked by counting colonies on the streptomycin plates and comparing with numbers of colonies on plates without streptomycin. The frequency of streptomycin resistant colonies should increase if the mutagenesis has worked satisfactorily. Furthermore, the number of colonies on plates without streptomycin was used for calculating the CFU/ml in order to obtain 3000 colonies when plating the mutagenized culture on Q-trays (Genetix Ltd., UK) for picking by an automated colony picker.

Q-trays contained MRS agar and were incubation at 37° C. over night anaerobically. Colonies were transferred by the colony picker to microtiter plates for assessment of acidification activity in milk.

b) Assay for Assessment of Acidification Activity of Mutants in Microtiter Plates During Screening Process Milk used for acidification experiments was prepared from 9.5% skim milk powder rehydrated in water and subsequently heat treated at 140° C./8 sec and 100° C./30 min.

Microtiter plates (384 wells) with milk containing 0.0476 mg/ml bromocresol purple (Na-salt) and 0.0476 mg/ml bromocresol green (Na-salt) was used for screening for mutants unable to grow in milk (method see WO2005/068982). Microtiter plates were incubated at 37° C. over night, anaerobically. If the milk changed color from blue to yellow, the strain was able to grow and made acid from lactose hence acidifying the media. If the color of milk stayed blue the strain was not able to produce acid in milk.

Stability of the non-acidifying isolates was tested by re-stricking 3 times on indicator-milk agar plates: Agar plates were prepared from milk containing 0.0476 mg/ml bromocresol purple (Na-salt) and 0.0476 mg/ml bromocresol green (Na-salt) as described above. 3.375 g bacto agar were dissolved in 25 ml milliQ water and added to 200 ml of hot indicator milk. The isolates were incubated at 37° C. and it was verified that the non-acidifying isolates did not start acidifying, but stayed blue in color (pH indicator) and grew poorly on the indicator milk plates. The mother strain DSM19500 turned yellow on the indicator milk agar plates.

c) Assessment of Proteinase Activity

The selected isolates, unable to grow in milk, were inoculated in a 96-well microtiter plate containing MRS media. The microtiter plate was incubated at 37° C., anaerobically over night.

The cell-wall associated proteinase activity was determined in a liquid handling robot as described below:

Solution A: 100 mM MES buffer, pH 5.5 containing 50 mM $CaCl_2$ (19.52 g MES and 7.35 g $CaCl_2$. Add water to 800 ml, adjust pH to 5.5 with 1 M HCl. Fill with water to 1000 ml)

Solution B: 5 mg/ml FITC-labeled casein (Sigma C3777), prepared in Milli-Q water Solution C: 5% w/v TCA (5 g TCA. Add Milli-Q water to 100 ml) Solution D: 500 mM Tris-HCl, pH 8.5 (60.55 g Tris-HCl. Add water to 800 ml, adjust pH to 8.5 with 1 M HCl. Fill with water to 1000 ml)

Microtiter plates: Nunc (Product no. 167008), Nunc Black (Product no. 237105), MJR PCR plate (V-shaped, product no. HSP-9665)

Tecan Liquid Handling Robot with 8- and 96-pipetting units, fluorescence/absorbance reader (Genious or Vic2), Galaxy incubator, two robotic arms, cooling units and a microtiter-plate centrifuge 1. The microtiter plate was centrifuged (2200 rpm. for 2 minutes, 6° C.) and 180 µl supernatant was aspirted to waste. The cells were resuspended in 180 µl solution A (precooled to 4° C.). This washing step was repeated once more.
2. 4 µl of FITC-labeled casein (precooled to 4° C.) were dispensed to a MJR PCR microtiter plate.
3. 20 µl of cell suspension were dispensed to the MJR PCR microtiter plate. The MJR PCR microtiter plate was incubated for 3 hours or 6 hours at 37° C. (one microtiter plate per incubation time).
4. 57.5 µl of solution C were dispensed to the MJR PCR microtiter plate. The MJR PCR microtiter plate was incubated for 1 hour at room temperature. The MJR PCR microtiter plate (2200 rpm. for 2 minutes, 6° C.) was centrifuged and 45 µl were dispensed from the MJR PCR microtiter plate to a Nunc Black microtiter plate. 125 µl of solution D were aspirated to the Nunc Black microtiter plate and mixed.
5. The fluorescence was read (Genious reader) of the Nunc Black microtiter plate using excitation and emission wavelengths of 485 and 535 nm, respectively.

At the same time the optical density of the washed cell suspensions is determined: 20 µl of three times washed and finally resuspended cells from step 1. were aspirated to a Nunc microtiter plate. 80 µl of solution A was added to the Nunc microtiter plate and mixed. Optical density was measured of the cell suspensions at 595 nm.

Figure 1:
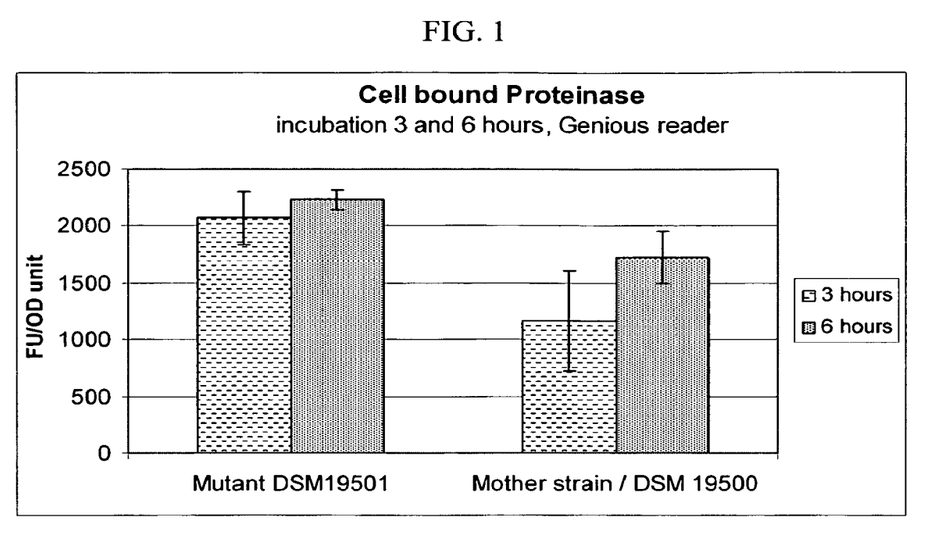
FIG. 1 depicts the cell wall bound proteinase activity of wild type and one mutant of Lb. helveticus DSM19500. The cell wall-associated proteinase activity is shown as specific activity (Fluorescence units/OD unit), cf. the example 1.

FIG. 1 shows the cell wall bound proteinase activity of wild the type strain *Lactobacillus helveticus* DSM19500 and the mutant DSM19501. The cell wall-associated proteinase activity is shown as specific activity (Fluorescence units/OD unit). Per strain, 8 independent growing subcultures were made and standard deviations are given for these 8 replicates per strain.

It was shown that the non-acidifying mutant DSM19501 has comparable cell wall bound proteinase activity than the mother strain.

Example 2

Assessment of Acidification Activity of Mutants by Direct pH Measurement in Milk As a start, working ampoules were made by incubating the strains in MRS broth at 37° C. over night. The pH was adjusted to pH 6.2 with NaOH and 20% sterilized Glycerol. The ampoules of each strain were stored frozen at −80° C. The strains were inoculated from the frozen ampoules at 1% v/v into MRS growth medium and incubated at 37° C. over night to obtain $1.5 \times 10^6$ cfu/ml.

2 ml of the over night culture were inoculated in 200 ml milk and incubated at 37° C. Milk used for acidification experiments was prepared from 9.5% skim milk powder rehydrated in water and subsequently heat treated at 140° C./8 sec and 100° C./30 min. pH was measured continuously with pH probes connected to a datalogger.

Figure 2:
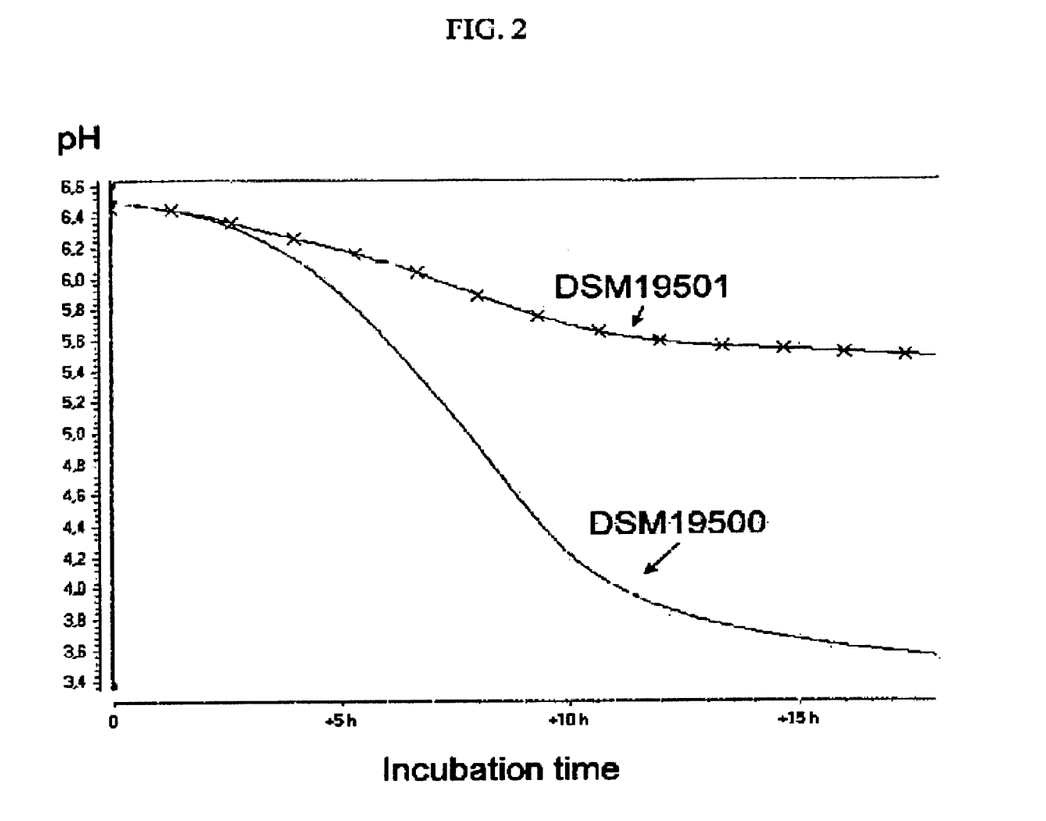
FIG. 2 depicts the acidification profile in milk of the mother stain *Lactobacillus helveticus* DSM19500 and *Lactobacillus helveticus* mutant strain DSM19501, cf. the example 2.

The mother strain acidified down to pH 4.2 at 10 hours whereas the non-acidifying strain stayed at higher pH (see FIG. 2).

Example 3

Use of Non-Acidifying *Lactobacillus Helveticus* Mutant DSM19501 as Adjunct Culture in the Production of Cheddar Cheese Cheddar cheeses (50% fat in dry matter and 54% moisture in non-fat substance) were made from pasteurized (72° C. for 15 s) bovine milk using chymosin (CHY-MAX™ Plus, Chr. Hansen A/S) and a frozen Cheddar-starter culture F-DVS RST-630 composed of *Lactococcus lactis* supsp. *lactis* and *Streptococcus thermophilus* (0.008% w/w F-DVS RST630, Chr. Hansen A/S).

Experimental cheeses were made with the starter culture alone, in combination with *Lactobacillus helveticus* mother strain DSM19500 or in combination with the non-acidifying *Lactobacillus helveticus* mutant strain DSM19501 respectively. The inoculation level of the *Lactobacillus helveticus* strains was $6 \times 10^6$ cfu/ml milk.

The manufacturing method used was as previously described (conventional cheese manufacture) with a starter inoculation at 32° C., a pre-ripening time of 45 minutes and a setting time of 45 minutes. The coagulum was cut in cubes (5×5×5 mm), stirred for 15 min and then temperature increased to 40° C. in 40 minutes. Afterwards scalding agitation continued for further 20 minutes. Then the whey was drained off and the curd was further drained until pH of 5.2 5.3 was reached. The curd was milled, salted and filled into moulds. The cheeses were pressed in molds for 17 hours. One cheese of about 14 kg was obtained from each vat of 150 kg vat milk.

After pressing the cheeses were removed from the moulds and vacuum packed in Cryovac® BL1L plastic bags (Cryovac, St. Neots, Belgium) and stored at 9° C. for a defined storage time.

The evolution of pH values was followed during cheese make as shown below:

| Step in manufacture | Time [hours] after culture addition | Control cheese without adjunct | Cheese with adjunct cultre mutant DSM19501 | Cheese with adjunct culture mother strain DSM19500 |
| --- | --- | --- | --- | --- |
| Add milk | 0:00 | 6.62 | 6.62 | 6.62 |
| Whey off | 2:45 | 6.39 | 6.35 | 6.31 |
| 2. turn | 3:20 | 5.85 | 5.79 | 5.74 |
| 3. turn | 3:40 | 5.59 | 5.54 | 5.45 |
| 4. turn | 4:05 | 5.39 | 5.36 | 5.24* |
| 5. turn | 4:15 | 5.34 | 5.27* | |
| 6. turn | 4:30 | 5.29* | | |
| 1 week old cheese | | 5.26 | 5.26 | 5.08 |

*milling pH reached

Milling pH was reached 25 minutes earlier when the *Lactobacillus helveticus* mother strain DSM19500 was used as adjunct in comparison to the reference cheese without use of *Lactobacillus helveticus* adjunct culture.

Figure 3:
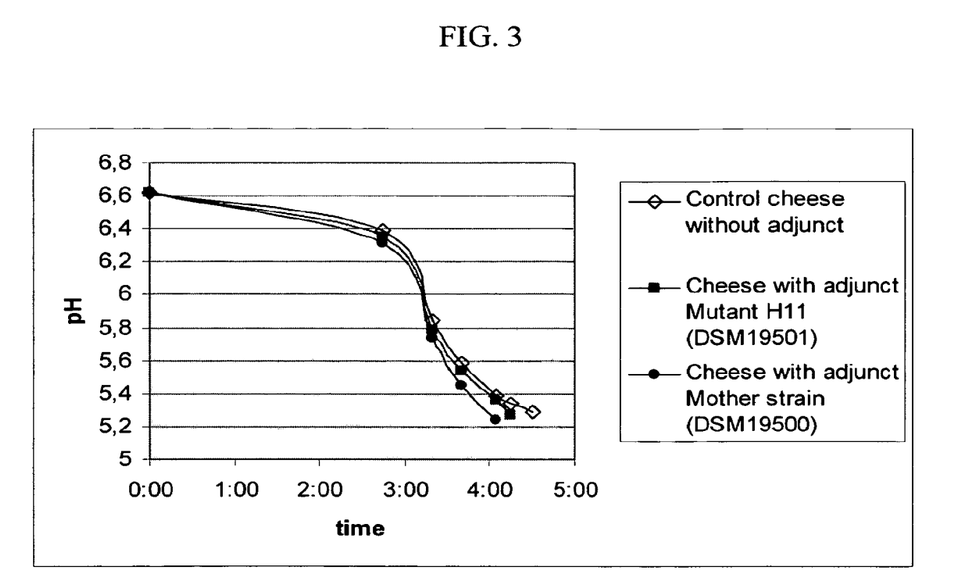
FIG. 3 depicts the acidification profile during cheese make of control cheese, cheese made with the mother stain *Lactobacillus helveticus* DSM19500 as adjunct and cheese made with *Lactobacillus helveticus* mutant strain DSM19501 as adjunct, cf. the example 3.

The use of the non-acidifying mutant DSM19501 had only minor influence on milk acidification, see FIG. 3.

The pH at 1 week age was significantly lower in the cheese made with the *Lactobacillus helveticus* mother strain DSM19500 as adjunct.

Sensory Evaluation

An expert panel (5 panelists) evaluated the cheeses organoleptically after 10 weeks of ripening. The trays with cheese samples were tempered in a thermostatic upboard at 12° C. before the sensory evaluation. The panelists were asked to rate each cheese on a 15 cm undifferentiated scale for each sensory attribute (0 being low intensity and 15 being high intensity). The control cheese made without adjunct culture was the reference cheese for sensory profiling. A consensus sensory profile of the reference cheese was established first.

Than the two cheeses containing adjunct cultures and the control cheese without adjunct culture were evaluated. A randomized three-digit identification code was given to each of the samples. Consensus profile of each cheese was established in comparison to the reference. The values given for the control cheese in the table below are averages of the first profiling as reference cheese and the second evaluation among the coded samples.

Flavour profiles of Cheddar cheeses at 10 weeks age (scale 0-15 cm)

| | Control cheese without adjunct culture | Cheese with adjunct culture DSM19501 | Cheese with adjunct culture DSM19500 |
| --- | --- | --- | --- |
| Boiled milk | 6.50 | 6.00 | 4.00 |
| Whey | 4.00 | 4.00 | 4.00 |
| Milk fat | 9.13 | 4.00 | 6.50 |
| Sulfur | 2.75 | 2.75 | 1.50 |
| Brothy | 5.50 | 5.25 | 7.75 |
| Farmhouse | 4.00 | 4.25 | 5.25 |
| Sour | 6.50 | 6.50 | 6.50 |
| Bitter | 5.25 | 4.00 | 3.50 |
| Salt | 5.63 | 6.50 | 7.75 |
| Sweet | 4.63 | 6.50 | 7.50 |

Figure 4:
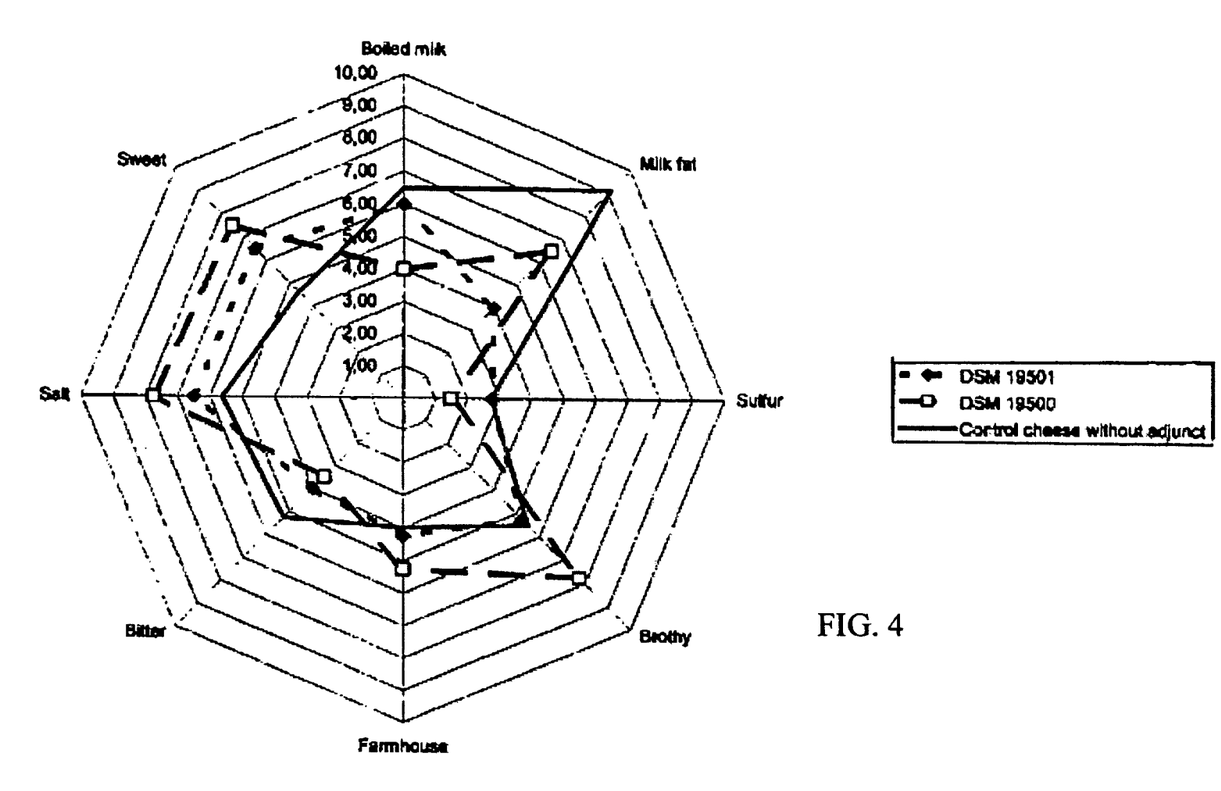
FIG. 4 depicts the flavour profile of control cheese, cheese made with *Lactobacillus helveticus* mother strain DSM19500 and cheese made with *Lactobacillus helveticus* mutant strain DSM19501, cf. the example 3.

The flavour profiles of the three cheeses (except descriptors "whey" and "sour" having the same values for all three cheeses) are shown in FIG. 4.

The control cheese made without adjunct culture was related to the sensory descriptors "boiled milk", "bitter" and "milk fat". In contrast, the two cheeses made with adjunct *Lactobacillus helveticus* strains were different from the control cheese. Sensory descriptors like "salty" and "sweet" dominated more and those cheeses were described as significantly less bitter than the control cheese.

It was thereby demonstrated that non-acidifying *Lactobacillus helveticus* strains can be successfully used as adjunct cultures to improve flavour and/or texture and/or taste in cheese.

The invention claimed is:

1. A process for improving the texture and/or taste and/or flavor of cheese, comprising:
    adding to milk
        a lactic acid bacteria culture comprising a strain belonging to a genus selected from the group consisting of *Lactococcus, Leuconostoc, Pediococcus, Streptococcus, Lactobacillus*, and *Enterococcus*, and
        a non-attenuated, non-acidifying *Lactobacillus helveticus* strain selected from *Lactobacillus helveticus* strain DSM 19501 deposited at the Deutsche Sammlung von Mikroorganismen and Zellkulturen GmBH (DSMZ) and mutants thereof, wherein the non-attenuated, non-acidifying *Lactobacillus helveticus* strain has at least as high cell wall bound protease activity as acidifying *Lactobacillus helveticus* strain DSM 19500 deposited at the DSMZ, and is not able to lower the pH more than 1.5 pH units from a starting pH of 6.5 after 10 hours incubation at 37° C. when inoculated from a fresh over-night culture at an inoculation dose of $1.5 \times 10^7$ cfu/ml into 200 ml of milk, and
        a coagulant;
    and then heating the resultant mixture to a temperature in the range of 30 to 45° C.

2. The process of claim 1, further comprising, after heating the mixture to a temperature in the range of 30 to 45° C., holding the mixture at that temperature range for 5 to 70 minutes immediately before whey removal or pre-pressing under whey.

3. The process of claim 1, wherein the non-attenuated, non-acidifying *Lactobacillus helveticus* strain is not able to lower the pH more than 1.5 pH units from a starting pH of 6.5 after 10 hours incubation at 37° C. when inoculated from a fresh over-night culture at an inoculation dose of $1.5 \times 10^7$ cfu/ml into 200 of ml milk prepared from 9.5% skim milk powder rehydrated in water and heat treated at 140° C./8 sec and 100° C./30 min.

4. The process of claim 3, wherein the non-attenuated, non-acidifying *Lactobacillus helveticus* strain is not able to lower the pH more than 1.3 pH units from a starting pH of 6.5 after 10 hours incubation at 37° C. when inoculated from a fresh over-night culture at inoculation dose $1.5 \times 10^7$ cfu/ml into 200 ml of milk.

5. The process of claim 1, wherein the non-attenuated, non-acidifying *Lactobacillus helveticus* strain is the strain DSM 19501.

6. The process according to claim 1, wherein the lactic acid bacteria culture comprises a strain selected from the group consisting of *Lactococcus lactis, Leuconostoc mesenteroides, Pediococcus pentosaceus, Lactobacillus casei, Lactobacillus paracasei, Streptococcus thermophilus, Enterococcus faecium, Lactobacillus delbrueckii* subsp. *bulgaricus, Lactobacillus delbrueckii* subsp. *lactis* and *Lactobacillus acidophilus*.

7. The process of claim 1, wherein the cheese is a cheddar type cheese or a continental type cheese.

8. A cheese obtained by the process of claim 1.

9. The process of claim 1, wherein the coagulant comprises a milk clotting enzyme.

10. The process of claim 1, wherein the cheese is a low-fat cheese.

11. The cheese of claim 8, wherein the cheese is a cheddar type cheese.

12. The cheese of claim 8, wherein the cheese is a continental type cheese.

13. The cheese of claim 8, wherein the cheese is a low-fat cheese.

14. The process of claim 1, wherein the non-attenuated, non-acidifying *Lactobacillus helveticus* strain is a mutant of the strain DSM 19501 deposited at DSMZ, wherein the mutant has at least as high cell wall bound protease activity as the acidifying *Lactobacillus helveticus* strain DSM 19500 deposited at DSMZ and is not able to lower the pH more than 1.5 pH units from a starting pH of 6.5 after 10 hours incubation at 37° C. when inoculated from a fresh over-night culture at an inoculation dose of $1.5 \times 10^7$ cfu/ml into 200 ml of milk.

* * * * *

UNITED STATES PATENT AND TRADEMARK OFFICE
CERTIFICATE OF CORRECTION

| | | |
|---|---|---|
| PATENT NO. | : 11,241,019 B2 | Page 1 of 1 |
| APPLICATION NO. | : 14/789623 | |
| DATED | : February 8, 2022 | |
| INVENTOR(S) | : Rattray et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

Signed and Sealed this
Twenty-ninth Day of November, 2022

Katherine Kelly Vidal
*Director of the United States Patent and Trademark Office*